United States Patent
Dong et al.

(10) Patent No.: US 10,877,012 B2
(45) Date of Patent: *Dec. 29, 2020

(54) AUTOMATIC SITING FOR AIR QUALITY MONITORING STATIONS

(71) Applicant: International Business Machines Corporation, Armonk, NY (US)

(72) Inventors: Jin Dong, Beijing (CN); Xiao Guang Rui, Beijing (CN); Jian Yao, Beijing (CN); Wen Jun Yin, Beijing (CN); Chao Zhang, Beijing (CN); Xin Zhang, Beijing (CN); Yu Xin Zhao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/567,172

(22) Filed: Sep. 11, 2019

(65) Prior Publication Data

US 2020/0003742 A1    Jan. 2, 2020

Related U.S. Application Data

(62) Division of application No. 15/494,759, filed on Apr. 24, 2017, now Pat. No. 10,725,008.

(51) Int. Cl.
*G01N 33/00* (2006.01)
*G01N 1/22* (2006.01)
(Continued)

(52) U.S. Cl.
CPC ....... *G01N 33/0075* (2013.01); *G01N 1/2273* (2013.01); *G01N 15/06* (2013.01);
(Continued)

(58) Field of Classification Search
None
See application file for complete search history.

(56) References Cited

U.S. PATENT DOCUMENTS

2002/0016835 A1    2/2002    Gamerman
2002/0084655 A1    7/2002    Lof et al.
(Continued)

OTHER PUBLICATIONS

Hsieh, H-P., et al., "Inferring Air Quality for Station Location Recommendation Based on Urban Big Data", Proceedings of the 21st ACM SIGKDD International Conference on Knowledge Discovery and Data Mining, pp. 1-10. Aug. 10, 2015.
(Continued)

*Primary Examiner* — Tung S Lau
(74) *Attorney, Agent, or Firm* — Fleit Intellectual Property Law; Jose Gutman (57) ABSTRACT

A system, a computer readable storage medium, and a method for automatically siting for air quality monitoring stations includes collecting from air quality monitoring stations air pollution concentration data, collecting from meteorological stations meteorological data, and interpolating, by the at least one or more processors, the air pollution concentration data to provide interpolated air pollution concentration data. The method and system can further cluster the interpolated air pollution concentration data and the meteorological data to provide clustered data and select a candidate site for an air monitoring station using the clustered data. The method and system can further evaluate a relationship of the air pollution concentration data with the meteorological data by weighting the air pollution data with the meteorological data.

18 Claims, 9 Drawing Sheets

(51) Int. Cl.
  *G01N 35/00* (2006.01)
  *G01N 15/06* (2006.01)
  *G01N 15/00* (2006.01)
(52) U.S. Cl.
  CPC ... *G01N 33/0022* (2013.01); *G01N 35/00871* (2013.01); *G01N 2015/0046* (2013.01); *G01N 2035/00881* (2013.01)

(56) References Cited

U.S. PATENT DOCUMENTS

| | | | | |
|---|---|---|---|---|
| 2006/0015254 | A1* | 1/2006 | Smith | H04W 4/024 |
| | | | | 702/3 |
| 2013/0013206 | A1 | 1/2013 | Guha et al. | |
| 2013/0324154 | A1* | 12/2013 | Raghupathy | G01S 5/0236 |
| | | | | 455/456.1 |
| 2013/0325878 | A1* | 12/2013 | de Lichana | G06F 16/22 |
| | | | | 707/748 |
| 2016/0125307 | A1 | 5/2016 | Zheng et al. | |
| 2016/0370333 | A1* | 12/2016 | Li | G01N 33/0004 |
| 2017/0249056 | A1* | 8/2017 | Rainey | G06F 3/04842 |
| 2018/0240057 | A1* | 8/2018 | Ba | G06Q 10/06313 |
| 2018/0306762 | A1* | 10/2018 | Dong | G01N 35/00871 |
| 2019/0149365 | A1* | 5/2019 | Chatterjee | H04L 5/0092 |
| | | | | 370/329 |
| 2019/0339416 | A1* | 11/2019 | Elkabetz | G01W 1/02 |

OTHER PUBLICATIONS

Non-Final Office Action for U.S. Appl. No. 15/494,759 dated Feb. 6, 2019.
Notice of Allowance for U.S. Appl. No. 15/494,759 dated Jul. 19, 2019.
List of IBM Patents or Patent Applications Treated as Related Sep. 11, 2019.

* cited by examiner

AUTOMATIC SITING FOR AIR QUALITY MONITORING STATIONS

BACKGROUND

The present disclosure generally relates to a computer system and method, and more particularly relates to a system and method for automatic siting for air quality monitoring stations.

Existing techniques including existing computer systems are generally not ideally suited for accurately detecting and placing air quality monitoring stations. Air pollution is a serious problem for many developing countries including China that will negatively impact national health and economic conditions. Current techniques for placement of monitoring stations typically involve the manual consultation with experts, which is a time consuming and inaccurate process particularly for a system with a vast number of monitoring stations.

Air quality stations are used for air pollution monitoring and prevention and can assist in determining the space distribution as relating to the source of the pollution, in guiding human activities that impact pollution, and for forecasting the extent of the pollution.

SUMMARY

According to one embodiment of the present invention, a method for automatically siting for air quality monitoring stations includes collecting from air quality monitoring stations air pollution concentration data, collecting from meteorological stations meteorological data, and interpolating, by the at least one or more processors, the air pollution concentration data to provide interpolated air pollution concentration data. The method and system can further cluster the interpolated air pollution concentration data and the meteorological data to provide clustered data and select a candidate site for an air monitoring station using the clustered data. The method and system can further evaluate a relationship of the air pollution concentration data with the meteorological data by weighting the air pollution data with the meteorological data.

According to another embodiment of the present invention, a system for automatically siting for air quality monitoring stations can include at least one memory and at least one processor of a computer system communicatively coupled to the at least one memory, the at least one processor, responsive to instructions stored in memory, and being configured to perform a method. The method can include collecting from an air quality monitoring stations, air pollution concentration data, collecting from meteorological stations, meteorological data, interpolating, by the at least one processor, at least the air pollution concentration data to provide interpolated air pollution concentration data, clustering, by the at least one processor, the interpolated air pollution concentration data and the meteorological data to provide clustered data, and selecting, by the at least one or more processors, a candidate site for an air monitoring station using the clustered data.

According to yet another embodiment of the present invention, a non-transitory computer readable storage medium can include computer instructions which, responsive to being executed by one or more processors, cause the processor or processors to perform operations as described in the methods or systems above or elsewhere herein.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

As required, detailed embodiments of the present invention are disclosed herein; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure and function. Further, the terms and phrases used herein are not intended to be limiting; but rather, to provide an understandable description of the invention.

According to various embodiments of the present invention, disclosed is a system and method for automatic siting for air quality monitoring stations. Air pollution is a severe problem for humanity causing potentially disastrous results from a health and economic standpoint for any number of countries. Measuring or monitoring the air quality is one of the primary steps in reducing and preventing air pollution. In the vast regions of a number of landmasses, the number of air quality monitoring stations and their placement is insufficient for monitoring air pollution metrics effectively. Furthermore, appropriately siting (or placing) the air quality monitoring stations efficiently for the best and most accurate results is challenging. In China and other developing countries, the situation is more urgent for national health and economic losses and the current methods of monitoring by consulting with experts are slow, inaccurate and inadequate. Air quality monitoring is the basis for air pollution prevention to assist in guiding future human activity, determining adequate space distribution which serves in detecting pollution sources in industry, and for air quality forecasting.

Embodiments of the invention generally leverage meteorological and air pollution concentration data as the basis of the siting as an objective input and evaluation for a different kind of air quality monitoring station selection or siting method. The siting methods can use clustering to find the potential candidate or backup station sites and can further use mathematical optimization methods to further refine the selection process. The embodiments can further combine meteorological data with the air pollution concentration data to help find the source and transmission patterns of the air pollutant. The embodiments also consider the change of the time into consideration for the evaluation of different station. The change of time can be seasonal (e.g., summer, autumn, winter, spring), or time of day, or day of the week, or day of the month, or any other time increment. The methods herein can also use clustering to find the typical sites for air quality monitoring evaluation and air pollutant transmission. In some embodiments, mathematical optimization techniques can optimize the selection of station sites and also use expert experience and common sense into constraints for use with the system. Other factors such as data regarding roads and terrain can also be used as inputs for constraints or for optimization for reasonable and practical outputs and solutions. The embodiments can be implemented so that siting is done rapidly and applied for a large number of monitoring stations. In other words, the methods and systems are scalable and can be extended from one area to another or from one city to another in a manner that is objective and reasonable.

The system is implemented as follows: 1. We Collect air pollution data from monitor stations and interpolate it in the dimensions of time and space. 2. We use clustering method to get the backup site for our selection. 3. The backup site will be much more than the stations we want to choose. And each of the backup sites will have an identification by expert experience and other reference. 4. The mathematical optimization method is used to get the solution of the stations. As the problem may be a NP-hard question, we may have an optimization function and some of constraints for iteration.

Figure 1:
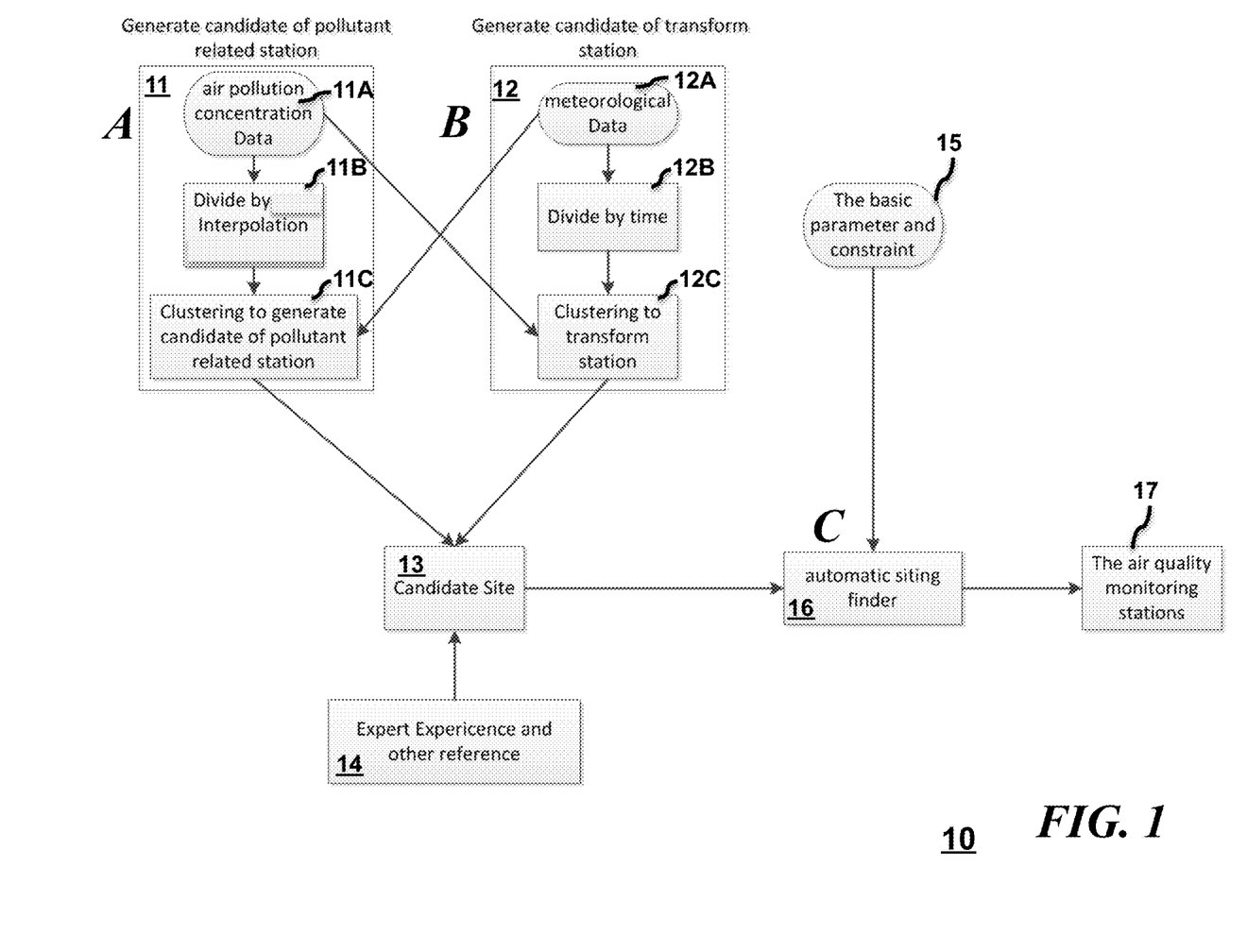
FIG. 1 is a depiction of flow diagram of a system or method for automatically siting for air quality monitoring stations according to various embodiments of the present invention.

A system or method 10 represented in FIG. 1 can include generating candidate air pollution monitoring stations at block 11 by collecting air pollution concentration data at 11A, interpolating the air pollution data in terms of time and space at block 11B, and clustering the interpolated data to generate the candidate air pollution monitoring stations at block 11C. Concurrently or non-concurrently, the system or method can generate candidates of meteorological monitoring stations (also referred to as "transform stations") at block 12 (that can monitor, for example, air pressure cells and locations, temperature, humidity, heat, heat indexes, UV indexes, dew points, precipitation, and other weather related data parameters). The meteorological data can be collected at block 12A, and sliced or divided by time at block 12B before clustering the potential meteorological monitoring stations at block 12C. The method can further evaluate the air pollution concentration data in view of the meteorological data for specific times and locations during the clustering steps in order to select a candidate site for an air quality monitoring station at block 13. Optionally, the method can use inputs from block 14 from expert experiential information, other historical data, or reference data to help in the selection of the candidate sites at block 13. All the candidate sites are gathered and collected at block 16 where an automatic siting finder makes appropriate selections among the candidate sites using basic parameters and constraints from block 15. The basic parameters and constraints can be user programmed or selected to suit a particular configuration and/or budget. The parameters or constraints can include one or more of a number of stations, a range of evaluation stations by percentage, range of reference stations by percentage, a range of highly polluting stations by percentage, a range of transform stations by percentage, or a minimum distance between every two stations. Other parameters and constraints can be included and selected as desired for a particular system. With the limitations set by the parameters and constraints from block 15, the automatic siting finder from block 16 can provide the selected air quality monitoring station (sites) at block 17.

Figure 2:
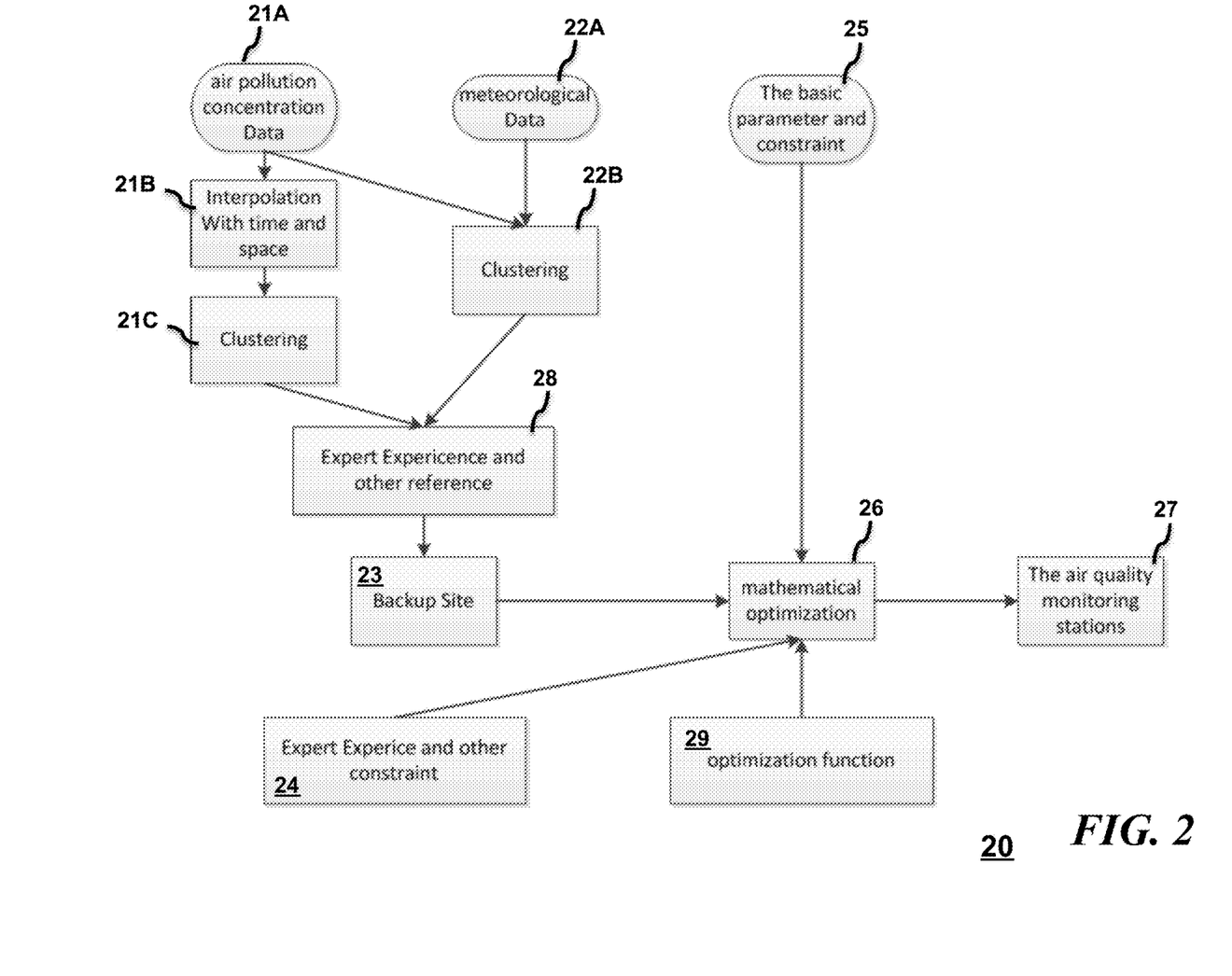
FIG. 2 is another depiction of flow diagram of a system or method for automatically siting for air quality monitoring stations according to various embodiments of the present invention.

A system or method 20 represented in FIG. 2 is similar to the system or method 10 of FIG. 1. The system or method 20 can include generating candidate air pollution monitoring stations by collecting air pollution concentration data at 21A, interpolating the air pollution data in terms of time and space at block 21B, and clustering the interpolated data at block 21C. Concurrently or non-concurrently, the system or method can generate candidates of meteorological monitoring stations or "transform stations" at block 22A and clustering the potential meteorological monitoring stations at block 22B. Optionally, the method 20 can use inputs from expert experiential information, other historical data, or reference data to help in the generation of the candidate or "backup" sites at block 23.

All the candidate sites are gathered and collected at block 26 where a mathematical optimization can assist in selecting the appropriate air quality station (sites) at block 27. The mathematical optimization block 26 can be similar to the automatic siting finder 16 of FIG. 1. The mathematical optimization block 26 can optionally use expert experiential information and other constraints from block 24, basic parameters and constraints 25, and one or more optimization functions 29 to assist in selecting the air quality station sites at block 27. The basic parameters or constraints can include similar parameters and constraints as described with respect to block 15 of FIG. 1. The expert experiential information and other constraints from block 24 can include the number or range of stations, the number or range of transform stations, the number or range of transform traffic stations, the number or range of highly polluting stations, the number or range of reference stations, the number or range of evaluation stations, or the minimum distance between every 2 stations. Other parameters and constraints can be included and selected as desired for a particular system. With the limitations set by the parameters and constraints from blocks 24, 25, and/or 29, the mathematical optimization from block 26 can provide the selected air quality monitoring station (sites) at block 27.

Figure 3:
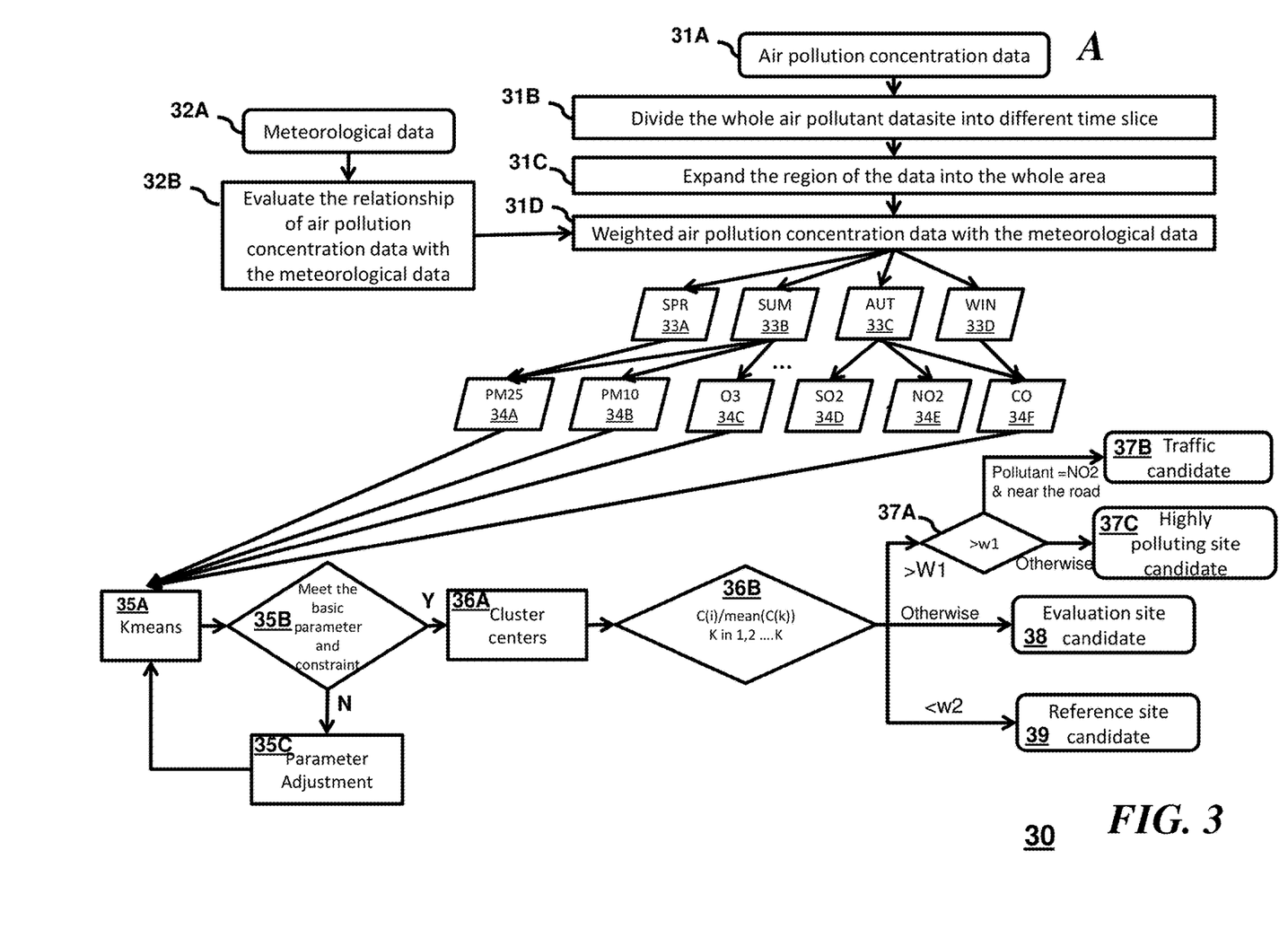
FIG. 3 is a depiction of flow diagram of a system or method for generating candidates of stations that monitor pollution concentration data according to various embodiments of the present invention.

Referring to FIGS. 1 and 3, a portion or section "A" of the overall method 10 in some embodiments involves generating the candidates of air pollution monitoring stations using the method 30 of FIG. 3. Method 30 collects the air pollution concentration data at 31A and further divides the air pollution concentration data into different time slices at 31B. The time sliced data of 31B can be applied or expanded to other areas of a particular overall area in a geographical interpolation at 31C. As previously described with respect to FIG. 1, meteorological data is gathered at 32A and evaluated with respect to the air pollution concentration data at block 32B. The air pollution concentration data can be weighted with the meteorological data and some stratification can be done in terms of time and in terms of types of pollutants for example. In this instance, the data can be stratified by seasons such as spring 33A, summer 33B, autumn, 33C, and winter 33D and by pollutants such as particles (PM25) 34A, particles (PM10) 34B, ozone (O3) 34C, sulfur dioxide (SO2) 34D, nitrogen dioxide (NO2) 34E, and carbon monoxide (CO) 34F.

The method can continue by clustering using, for example k-means clustering at block 35A. K-means clustering is a method of vector quantization; originally from signal processing that is popular for cluster analysis in data mining. K-means clustering aims to partition n observations into k clusters in which each observation belongs to the cluster with the nearest mean, serving as a prototype of the cluster. This results in a partitioning of the data space into cells known as Voronoi cells. Through an iterative process using decision block 35B that determines if the cluster meets the basic parameters and constraints set and through further parameter adjustments at block 35C, cluster centers are gathered at block 36A. Through a further decision block 36B comparing the concentration of one candidate station to the average of all the concentration of the candidate stations and a further stratification by weighting, the candidate sites can be selected by types. For example, if the weighting is greater than a first threshold w1 at 37A and the pollutant is determined to be nitrogen dioxide near a road, then the candidate site can be selected as a traffic candidate monitoring site at 37B and otherwise the candidate site can be selected as a highly polluting candidate site at 37C. If the weighting is less than the first threshold w1 and greater than a second threshold w2, then the candidate site can be selected as an evaluation site candidate at 38. If the weighing is less than the second threshold w2, then the candidate site can be selected as reference site candidate. The evaluation site candidate is generally considered a candidate site that can have some form of pollution, but generally not exceeding unacceptable limits but also not known for a generally pollutant free environment. The reference site candidate is generally considered a generally pollutant free environment or at least an environment with acceptable levels of pollutants to use as a reference in comparison to other sites.

The problem for selecting these sites is computationally difficult (NP-hard); however, there are efficient heuristic algorithms that can be employed to converge quickly to a local optimum. These are usually similar to the expectation-maximization algorithm for mixtures of Gaussian distributions via an iterative refinement approach employed by both algorithms Additionally, they both use cluster centers to model the data; however, k-means clustering tends to find clusters of comparable spatial extent, while the expectation-maximization mechanism allows clusters to have different shapes. The embodiments are not limited to using either clustering techniques and are only described herein as examples.

Figure 4:
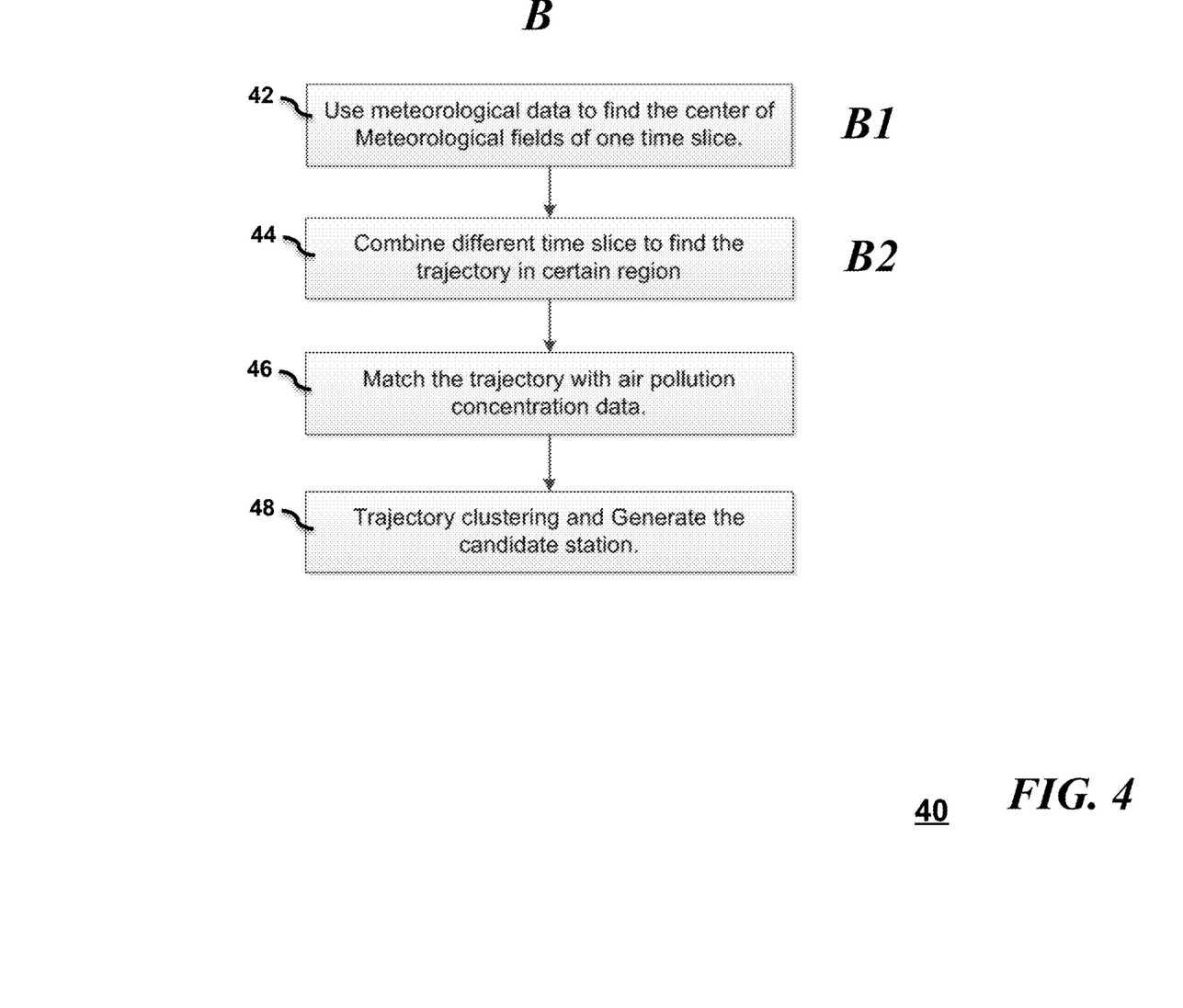
FIG. 4 is a depiction of flow diagram of a system or method for generating candidates of transform stations that monitor meteorological data according to various embodiments of the present invention.

Referring to FIGS. 1 and 4, a portion or section "B" of the overall method 10 in some embodiments involves generating the candidates of meteorological monitoring stations using the method 40 of FIG. 4. Method 40 uses the meteorological data at block 42 to find a center of meteorological fields of at least one time slice. In some embodiments, the meteorological fields can be pressure cells or measurements. The method 40 can further combine different time slices to find the trajectory in certain regions at block 44. At 46, the method 40 can then match the trajectory of the meteorological data with the air pollution concentration data. At 48, the method can then perform trajectory clustering and further generate the candidate air quality monitoring stations.

Figure 5A:
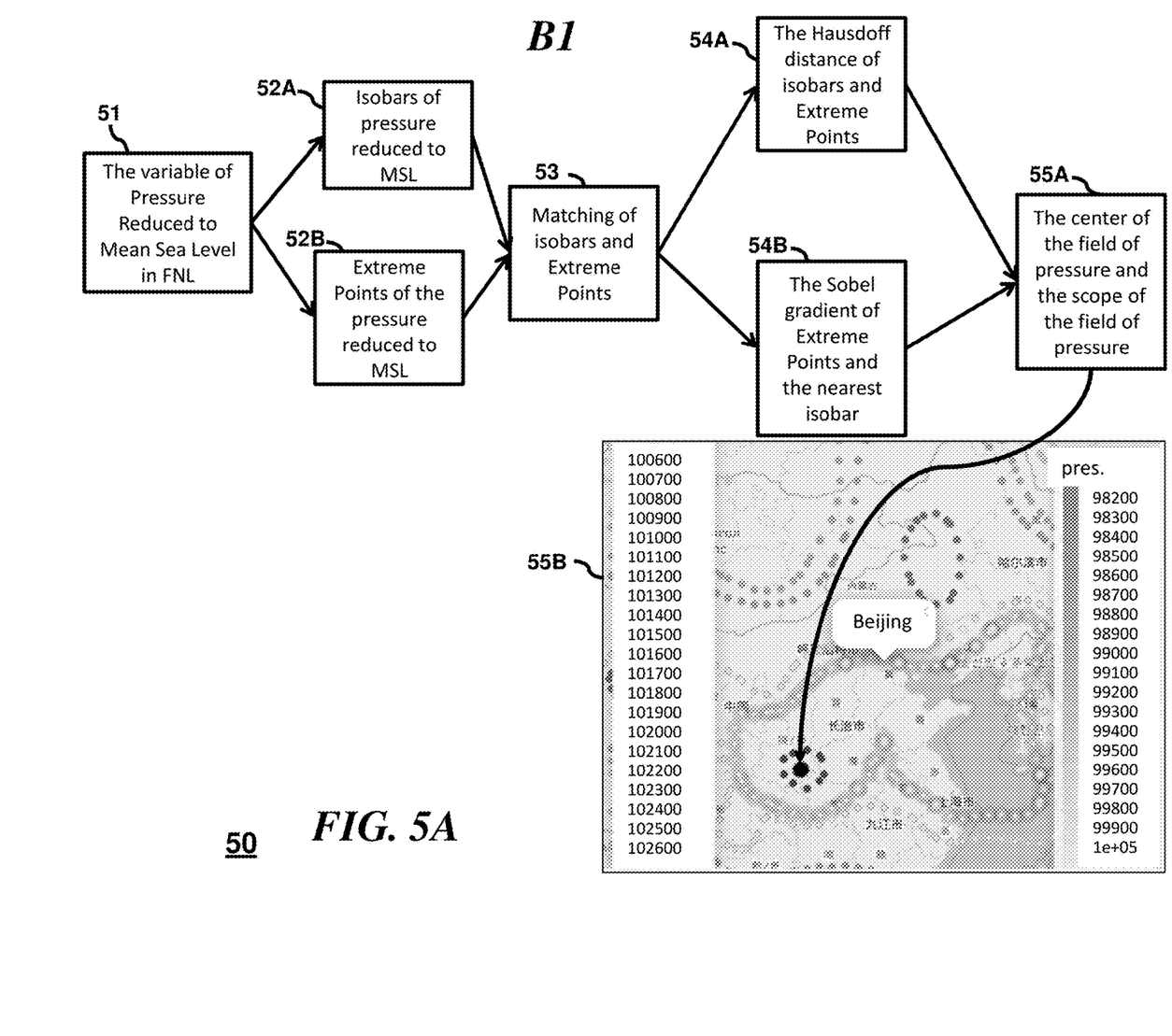
FIG. 5A is a flow diagram illustrating a method for using meteorological data to find a center of meteorological fields of a single time slice according to various embodiments of the present invention.

Referring to FIGS. 4 and 5A, a portion "B1" of the meteorological monitoring station candidate siting method 40 that finds the center of meteorological field of at least one time slice at block 42 is further detailed in method 50 of FIG. 5. At 51, a variable of the pressure is reduced to a Mean Sea Level (MSL) in a Final or FNL value. At 52A, the isobars of the pressure are reduced to a MSL value and at 52B, the extreme points of the pressure is reduced to a MSL value. Then, the isobars and extreme points are matched at block 53. At 54A, the Hausdoff distance of the isobars and the extreme points are determined and at 54B, the Sobel gradient of the extreme points and the nearest isobar are determined. Combining the metrics from 54A and 54B, a center of the field of pressure and the scope of the field of pressure is determined at 55A and can be represented in a map or presentation at 55B as shown.

Figure 5B:
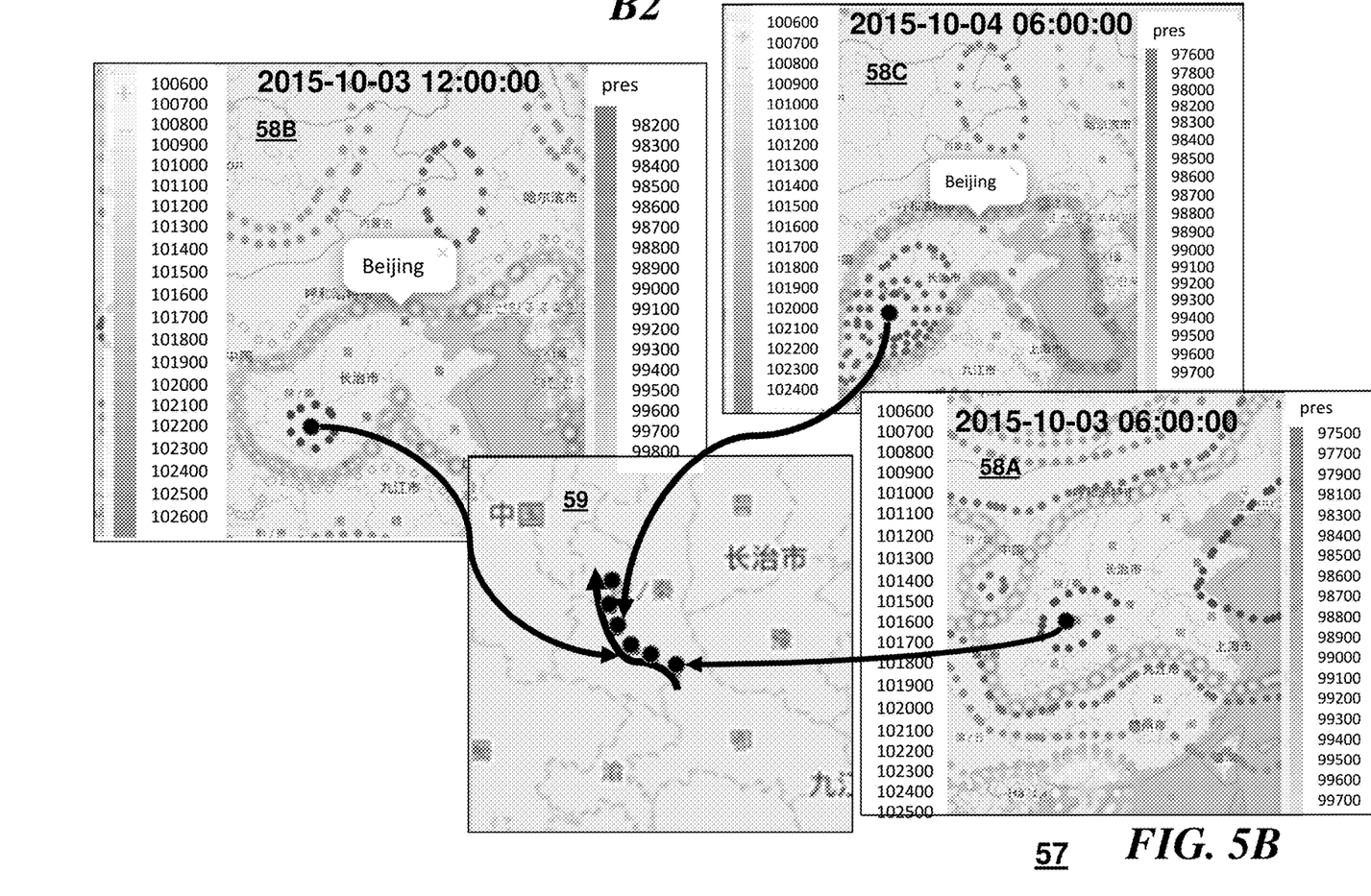
FIG. 5B is a flow diagram illustrating a method for combining different time slices to find a trajectory in a certain region according to various embodiments of the present invention.

Referring to FIGS. 4 and 5B, a portion "B2" of the meteorological monitoring station candidate siting method 40 that combines the different time slices to determine the trajectory of the meteorological data at block 44 is further illustrated by the representation 57 of FIG. 5B. FIG. 5B illustrates various time slices of maps including the time slice of 6:00:00 on Oct. 3, 2015 at 58A, the time slice of 12:00:00 on Oct. 3, 2015 at 58B and the time slice of 6:00:00 on Oct. 4, 2015 at 58C. These time slice representations are combined to determine and represent the trajectory of the meteorological data as illustrated by 59.

Figure 6:
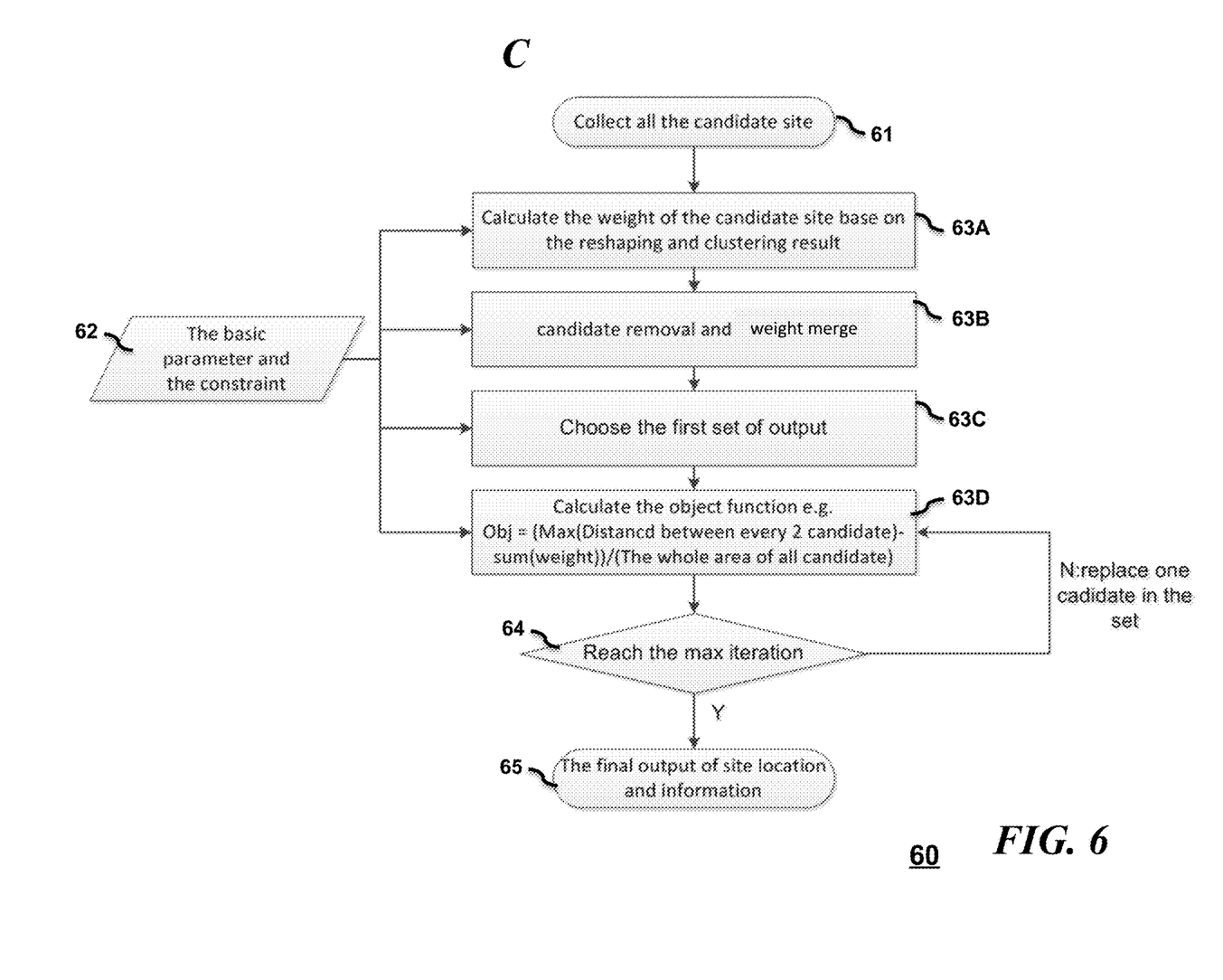
FIG. 6 is a flow diagram illustrating a method of automatic site finding according to various embodiments of the present invention.

Referring to FIGS. 1 and 6, a portion "C" of the overall method 10 in some embodiments involves a particular method of automatic site finding 60 similar in operation to the automatic siting finder 16 of FIG. 1. The method 60 begins by collecting all the candidate sites at 61 and applying basic parameters and constraints 62 to additional steps 63A-D as shown. More particularly, at 63A, a weight can be calculated for a given candidate site based on a reshaping and clustering result. Reshaping can be done in addition to clustering to further assist in selecting a candidate site based on the meteorological and pollution concentration data. At 63B, with the use of the basic parameters and constraints as well as the weighting information, some of the candidate sites can be removed and a first set of candidates can be provided at 63C. An optimization function can be further applied at 63D such as the function for calculating a object function, for example, Obj=(Max(Distance d between every 2 candidates)−sum (weight))/(The whole area of all candidates). The optimization function can be repeated at decision block 64 until a maximum iteration is reached. Once the maximum iteration is reached at block 64, the final output of the site location and corresponding information is provided at 65.

In some embodiments, a system includes at least one memory and at least one processor of a computer system communicatively coupled to the at least one memory. The at least one processor can be configured to perform a method including methods described above.

According yet to another embodiment of the present invention, a computer readable storage medium comprises computer instructions which, responsive to being executed by one or more processors, cause the one or more processors to perform operations as described in the methods or systems above or elsewhere herein.

Figure 7:
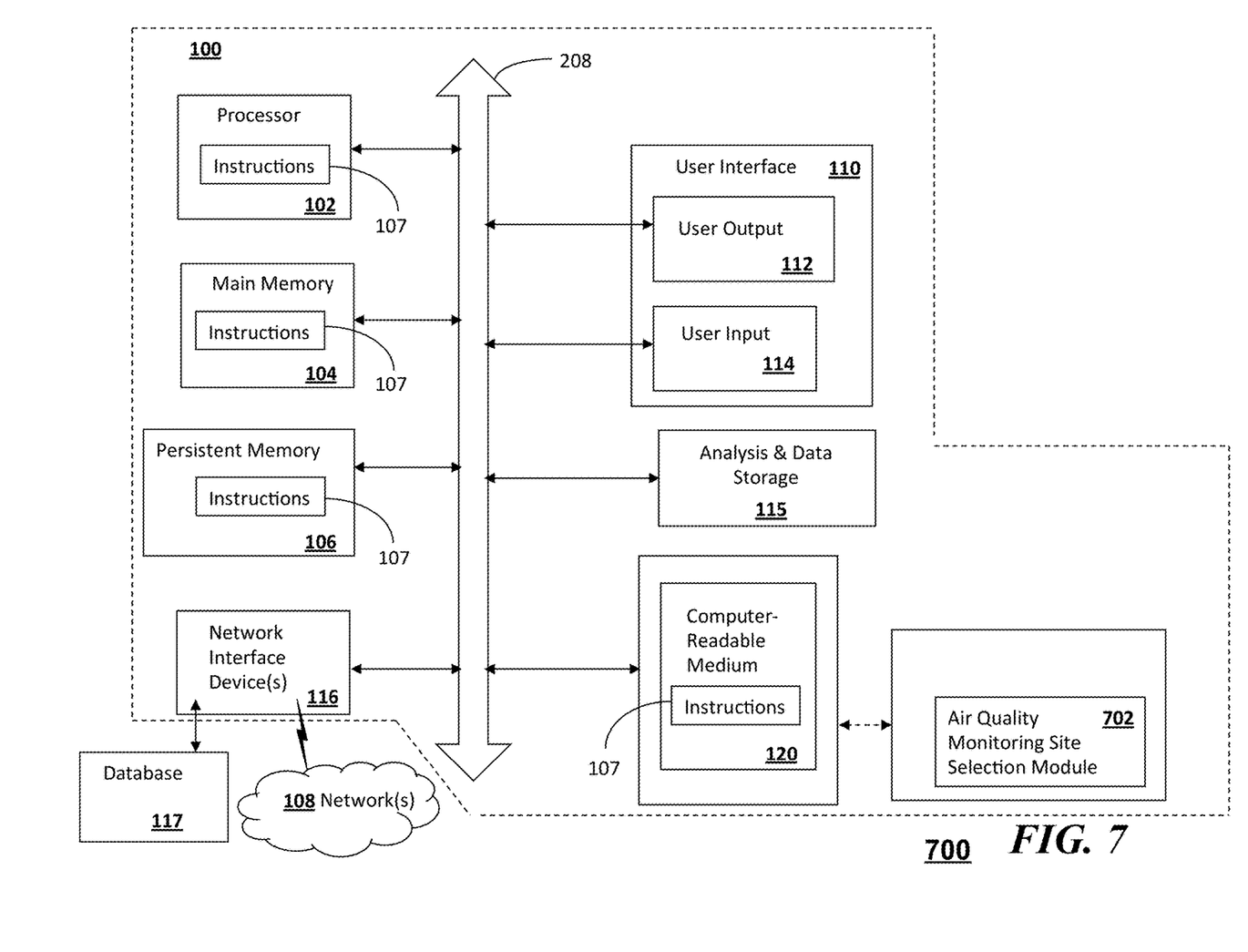
FIG. 7 is a block diagram illustrating a system automatically siting for air quality monitoring stations according to various embodiments of the present invention.

As shown in FIG. 37, an information processing system 100 of a system 700 can be communicatively coupled with the air quality monitoring site selection module 702 and a group of client or other devices, or coupled to a presentation device for display at any location at a terminal or server location. According to this example, at least one processor 102, responsive to executing instructions 107, performs operations to communicate with the site selection module 702 via a bus architecture 208, as shown. The at least one processor 102 is communicatively coupled with main memory 104, persistent memory 106, and a computer readable medium 120.

The processor 102 is communicatively coupled with an Analysis & Data Storage 115 that, according to various implementations, can maintain stored information used by, for example, the site selection module 702 and more generally used by the information processing system 100. Optionally, for example, this stored information can include information received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The site selection module 702, and the information processing system 100, can use the information from the history log such as in the analysis process and in making decisions related determining similarity and to retrieving similar images.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 100 includes a user interface 110 that comprises a user output interface 112 and user input interface 114. Examples of elements of the user output interface 112 can include a display, a speaker, one or more indicator lights, one or more transducers that generate audible indicators, and a haptic signal generator. Examples of elements of the user input interface 114 can include a keyboard, a keypad, a mouse, a track pad, a touch pad, a microphone that receives audio signals, a camera, a video camera, or a scanner that scans images. The received audio signals or scanned images, for example, can be converted to electronic digital representation and stored in memory, and optionally can be used with corresponding voice or image recognition software executed by the processor 102 to receive user input data and commands, or to receive test data for example.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present invention. The network interface device 116 can provide a communication interface for the information processing system 100 to access the at least one database 117 according to various embodiments of the invention.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

Figure 8:
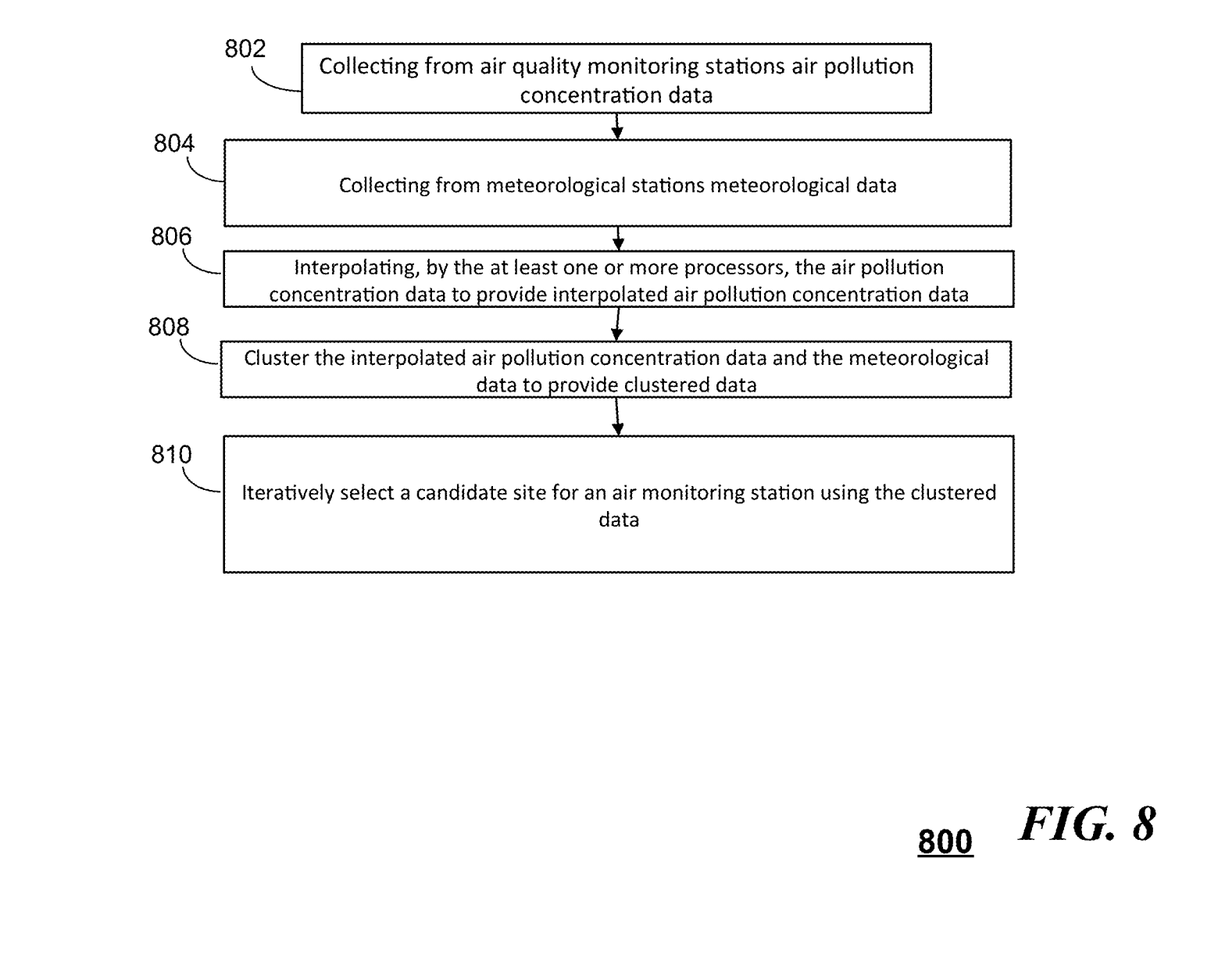
FIG. 8 is another depiction of flow diagram of a method for automatically siting for air quality monitoring stations according to various embodiments of the present invention.

FIG. 8 illustrates an example of a method, according to various embodiments of the present invention, which can operate in conjunction with the information processing system of FIG. 7. Specifically, according to the example shown in FIG. 8, a method 800 for siting air quality monitoring stations can include collecting air pollution concentration data from air quality monitoring stations at block 802 and collecting meteorological data from meteorological stations at 804. The method 800 can further include at block 806, interpolating the air pollution concentration data to provide interpolated air pollution concentration data. At block 808, the method can cluster the interpolated air pollution concentration data and the meteorological data to provide clustered data. At block 810, the method can iteratively select a candidate site for an air monitoring station using the clustered data. As part of the process, the candidate site can be qualified as one of a regular air quality monitoring station site as an evaluation site candidate (see 38 of FIG. 3), a reference site candidate (see 39 of FIG. 3), a traffic site candidate (see 37B of FIG. 3), or a highly polluting site candidate (see 37C of FIG. 3). Of course, the candidate site can be qualified as any other type of candidate site based on the parameters and stratification that a system designer can implement within contemplation of the various embodiments.

Non-Limiting Examples

The examples provide herein may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the invention is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this invention. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single example embodiment for the purpose of streamlining the invention. This method of invention is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor is illustrated for an information processing system, information processing systems with multiple CPUs or processors can be used equally effectively. Various embodiments of the present invention can further incorporate interfaces that each includes separate, fully programmed microprocessors that are used to off-load processing from the processor. An operating system (not shown) included in main memory for the information processing system may be a suitable multitasking and/or multiprocessing operating system, such as, but not limited to, any of the Linux, UNIX, Windows, and Windows Server based operating systems. Various embodiments of the present invention are able to use any other suitable operating system. Various embodiments of the present invention utilize architectures, such as an object oriented framework mechanism, that allows instructions of the components of operating system (not shown) to be executed on any processor located within the information processing system. Various embodiments of the present invention are able to be adapted to work with any data communications connections including present day analog and/or digital techniques or via a future networking mechanism.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The terms "communicatively coupled" or "communicatively coupling" include, but are not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A system comprising:
    a set of air quality monitoring stations individually placed and spaced apart at respective first set of locations in a defined geographic area to measure and monitor air pollution concentration data at the respective first set of locations, the set of air quality monitoring stations being communicatively coupled with a computer system;
    a set of meteorological stations individually placed and spaced apart at respective second set of locations in the defined geographic area to measure and monitor meteorological data at the respective second set of locations, the set of meteorological stations being communicatively coupled with the computer system;
    a network interface device;
    at least one memory; and
    at least one processor of a computer system communicatively coupled with the at least one memory, the network interface device, at least one air quality monitoring station in the set of air quality monitoring stations, and at least one meteorological station in the set of meteorological stations, and wherein the at least one processor, responsive to instructions stored in the at least one memory, being configured to perform a method comprising:
        collecting from the at least one air quality monitoring station in the set of air quality monitoring stations, air pollution concentration data at the respective location, in the first set of locations, of the at least one air quality monitoring station;
        collecting from the at least one meteorological station in the set of meteorological stations, meteorological data at the respective location, in the second set of locations, of the at least one meteorological station;

interpolating in time and space at least the air pollution concentration data collected at the respective first set of locations to provide interpolated air pollution concentration data for more locations than the respective first set of locations and expanded to locations over the defined geographic area;

clustering, by the at least one processor, the interpolated air pollution concentration data and the meteorological data to provide clustered data;

selecting, by the at least one processor, a candidate site for siting an air monitoring station using the clustered data by identifying a plurality of candidate sites and, for each time slice in a plurality of different time slices, a respective concentration of an air pollutant at each candidate site in the plurality of candidate sites in the defined geographic area respective first set of locations in a defined geographic area;

comparing, for each time slice in the plurality of different time slices, a concentration of the air pollutant at each candidate site to an average of all concentrations of the air pollutant at the plurality of candidate sites;

identifying, for each time slice in the plurality of different time slices, a center of meteorological fields in the defined geographic area;

identifying trajectory of centers of meteorological fields in the defined geographic area, based on combining time slices of clustered data of meteorological data;

selecting a candidate site from the plurality of candidate sites based on an atmospheric transmission pattern of the air pollutant that is identified with the identified trajectory of centers of meteorological fields and the concentration of the air pollutant at each candidate site in the plurality of candidate sites in the plurality of different time slices; and siting a location of an air quality monitoring station at the selected candidate site.

2. The system of claim 1, further comprising instructions stored in memory which when executed by the at least one processor causes the at least one processor to perform the operation of evaluating a relationship of the air pollution concentration data with the meteorological data by weighting the air pollution concentration data with the meteorological data.

3. The system of claim 1, wherein the instructions stored in memory which when executed by the at least one processor causes the at least one processor to perform the operation of weighting the meteorological data by time of the year and the air pollution data by type of pollutant.

4. The system of claim 1, wherein the instructions stored in memory which when executed by the at least one processor causes the at least one processor to perform the operations of using meteorological data to find a center of meteorological fields of one time slice, combining a different time slice to find a trajectory of a meteorological condition in a certain region, matching the trajectory with the air pollution concentration data and trajectory clustering, and generating at least one of the candidate sites.

5. The system of claim 1, wherein the instructions stored in memory which when executed by the at least one processor causes the at least one processor to perform the operation of automatically generating a center of a field of pressure and a scope of the field of pressure by matching isobars of pressure and extreme points of pressure, determining the Hausdoff distance of isobars and extreme points and determining the Sobel gradient of the extreme points and a nearest isobar.

6. The system of claim 5, wherein the instructions stored in memory which when executed by the at least one processor causes the at least one processor to further perform applying parameters and constraints to an automatic site finder after the automatic site finder receives all the candidate sites.

7. A non-transitory computer-readable storage medium having stored therein instructions which, when executed by at least one processor of a computer system, cause the at least one computer system to perform a method in a system which comprises a set of air quality monitoring stations individually placed and spaced apart at respective first set of locations in a defined geographic area to measure and monitor air pollution concentration data at the respective first set of locations, the set of air quality monitoring stations being communicatively coupled with the computer system, and a set of meteorological stations individually placed and spaced apart at respective second set of locations in the defined geographic area to measure and monitor meteorological data at the respective second set of locations, the set of meteorological stations being communicatively coupled with the computer system, the method comprising:

collecting from at least one air quality monitoring station in the set of air quality monitoring stations, air pollution concentration data at the respective location, in the first set of locations, of the at least one air quality monitoring station;

collecting from at least one meteorological station in the set of meteorological stations, meteorological data at the respective location, in the second set of locations, of the at least one meteorological station;

interpolating in time and space at least the air pollution concentration data collected at the respective first set of locations to provide interpolated air pollution concentration data for more locations than the respective first set of locations and expanded to locations over the defined geographic area;

clustering, by the at least one processor, the interpolated air pollution concentration data and the meteorological data to provide clustered data;

selecting, by the at least one processor, a candidate site for siting an air monitoring station using the clustered data by identifying a plurality of candidate sites and, for each time slice in a plurality of different time slices, a respective concentration of an air pollutant at each candidate site in the plurality of candidate sites in the defined geographic area respective first set of locations in a defined geographic area;

comparing, for each time slice in the plurality of different time slices, a concentration of the air pollutant at each candidate site to an average of all concentrations of the air pollutant at the plurality of candidate sites;

identifying, for each time slice in the plurality of different time slices, a center of meteorological fields in the defined geographic area;

identifying trajectory of centers of meteorological fields in the defined geographic area, based on combining time slices of clustered data of meteorological data; and selecting a candidate site from the plurality of candidate sites based on an atmospheric transmission pattern of the air pollutant that is identified with the identified trajectory of centers of meteorological fields and the concentration of the air pollutant at each candidate site in the plurality of candidate sites in the plurality of different time slices; and siting a location of an air quality monitoring station at the selected candidate site.

8. The non-transitory computer-readable storage medium of claim 7, further comprising weighting, by the at least one processor, the meteorological data by time of the year and the air pollution data by type of pollutant.

9. The non-transitory computer-readable storage medium of claim 7, further comprising automatically generating a center of a field of pressure and a scope of the field of pressure by matching isobars of pressure and extreme points of pressure, determining the Hausdoff distance of isobars and extreme points and determining the Sobel gradient of the extreme points and a nearest isobar.

10. The non-transitory computer-readable storage medium of claim 7, further comprising applying parameters and constraints to an automatic site finder after the automatic site finder receives all the candidate sites.

11. The non-transitory computer-readable storage medium of claim 10, wherein the applying parameters and constraints comprises calculating a weight of a candidate site based on a reshaping and clustering result, and iteratively calculating an object function to select a final output of the candidate site or candidate sites.

12. The non-transitory computer-readable storage medium of claim 10, wherein the parameters comprise one or more of a number of stations, a range of evaluation stations by percentage, a range of reference stations by percentage, a range of highly polluting stations by percentage, a range of transform stations by percentage, or a minimum distance between every two stations.

13. A non-transitory computer-readable storage medium having stored therein instructions which, when executed by at least one processor of a computer system, cause the at least one computer system to perform a method in a system which comprises a set of air quality monitoring stations individually placed and spaced apart at respective first set of locations in a defined geographic area to measure and monitor air pollution concentration data at the respective first set of locations, the set of air quality monitoring stations being communicatively coupled with the computer system, and a set of meteorological stations individually placed and spaced apart at respective second set of locations in the defined geographic area to measure and monitor meteorological data at the respective second set of locations, the set of meteorological stations being communicatively coupled with the computer system, the method comprising:

collecting from the set of air quality monitoring stations, air pollution concentration data at the respective first set of locations;

collecting from the set of meteorological stations, meteorological data at the respective second set of locations;

interpolating at least the air pollution concentration data collected at the respective first set of locations to provide interpolated air pollution concentration data for locations, other than the respective first set of locations, over the defined geographic area;

clustering, by the at least one processor, the interpolated air pollution concentration data and the meteorological data to provide clustered data;

selecting, by the at least one processor, a candidate site for siting an air monitoring station using the clustered data by identifying a plurality of candidate sites in the defined geographic area and, for each time slice in a plurality of different time slices, a respective concentration of an air pollutant at each candidate site in the plurality of candidate sites;

comparing, for each time slice in the plurality of different time slices, a concentration of the air pollutant at each candidate site to an average of all concentrations of the air pollutant at the plurality of candidate sites;

identifying, for each time slice in the plurality of different time slices, a center of meteorological fields in the defined geographic area;

identifying trajectory of centers of meteorological fields in the defined geographic area, based on combining time slices of clustered data of meteorological data; and selecting a candidate site from the plurality of candidate sites based on an atmospheric transmission pattern of the air pollutant that is identified with the identified trajectory of centers of meteorological fields and the concentration of the air pollutant at each candidate site in the plurality of candidate sites in the plurality of different time slices; and siting a location of an air quality monitoring station at the selected candidate site.

14. The non-transitory computer-readable storage medium of claim 13, wherein the interpolating comprises dividing the air pollution concentration data by time and applying time sliced data to different geographic areas.

15. The non-transitory computer-readable storage medium of claim 13, wherein the method further comprises using meteorological data to find a center of meteorological fields of one time slice, combining a different time slice to find a trajectory of a meteorological condition in a certain region, matching the trajectory with the air pollution concentration data and trajectory clustering, and generating at least one of the candidate sites.

16. The non-transitory computer-readable storage medium of claim 13, wherein the method further comprises automatically generating a center of a field of pressure and a scope of the field of pressure.

17. The non-transitory computer-readable storage medium of claim 13, wherein the method further comprises applying parameters and constraints to an automatic site finder after the automatic site finder receives all the candidate sites.

18. The non-transitory computer-readable storage medium of claim 13, wherein the method further comprises weighting the meteorological data by time of the year and the air pollution data by type of pollutant.

* * * * *